United States Patent
Ul Haq et al.

(10) Patent No.: US 10,299,694 B1
(45) Date of Patent: May 28, 2019

(54) METHOD OF CLASSIFYING RAW EEG SIGNALS

(71) Applicant: KING SAUD UNIVERSITY, Riyadh (SA)

(72) Inventors: Qazi Emad Ul Haq, Riyadh (SA); Muhammad Hussain, Riyadh (SA); Hatim Abdulrehman Aboalsamh, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 15/889,110

(22) Filed: Feb. 5, 2018

(51) Int. Cl.
| | |
|---|---|
| *A61B 5/04* | (2006.01) |
| *A61B 5/0476* | (2006.01) |
| *G16H 50/20* | (2018.01) |
| *A61B 5/00* | (2006.01) |

(52) U.S. Cl.
CPC .......... *A61B 5/0476* (2013.01); *A61B 5/7264* (2013.01); *G16H 50/20* (2018.01)

(58) Field of Classification Search
None
See application file for complete search history.

(56) References Cited

U.S. PATENT DOCUMENTS

| | | | |
|---|---|---|---|
| 8,298,140 B2 | 10/2012 | Beck-Nielsen et al. | |
| 2011/0028827 A1 | 2/2011 | Sitaram et al. | |
| 2013/0289944 A1 | 10/2013 | Ayesh | |
| 2015/0282755 A1 | 10/2015 | Deriche et al. | |

FOREIGN PATENT DOCUMENTS

WO 2017030539 A1 2/2017

OTHER PUBLICATIONS

Yazdani et al. "Classification of EEG signals correlated with alcohol abusers." Signal Processing and Its Applications, 2007. ISSPA 2007. 9th International Symposium on. IEEE, 2007.
Tomioka et al. "A regularized discriminative framework for EEG analysis with application to brain—computer interface." NeuroImage 49.1 (2010): 415-432.
Zhou et al. "Regularized matrix regression." Journal of the Royal Statistical Society: Series B (Statistical Methodology) 76.2 (2014): 463-483.
Bamatraf et al. "A system for true and false memory prediction based on 2D and 3D educational contents and EEG brain signals." Computational intelligence and neuroscience 2016 (2016): 45.
Emad-Ul-Haq et al. "Single Trial EEG Patterns for the Prediction of Individual Differences in Fluid Intelligence." Frontiers in Human Neuroscience 10 (2016).

*Primary Examiner* — Etsub D Berhanu
(74) *Attorney, Agent, or Firm* — Richard C. Litman

(57) ABSTRACT

The method of classifying raw EEG signals uses a classification method based on nuclear features extracted as dominant singular values from an EEG signal segment using singular value decomposition (SVD) and a class means-based minimum distance classifier (CMMDC) to classify a patient's EEG signals. From a mean EEG signal, a set of zero-centered EEG signals are calculated, and from the zero-centered EEG signals and a standard deviation of the EEG signals, a unit variance is calculated for each component. Using the standardized component signals a nuclear matrix is calculated, to which singular value decomposition is applied to generate a set of singular values. The CMMDC is applied to class means associated with first and second classes and a nuclear feature vector to classify the patient's EEG signals as belonging in either the first or second class.

2 Claims, 4 Drawing Sheets

METHOD OF CLASSIFYING RAW EEG SIGNALS

BACKGROUND

1. Field

The disclosure of the present patent application relates to the classification of electroencephalogram (EEG) signals, and particularly to a classification method based on nuclear features extracted as dominant singular values from an EEG signal segment using singular value decomposition (SVD) and a class means-based minimum distance classifier (CM-MDC) to classify a patient's EEG signals.

2. Description of the Related Art

A wide variety of electroencephalogram (EEG) feature extraction methods have been studied, such as transform-based approaches, spectral analysis, wavelet analysis, power analysis, entropy analysis, time-frequency analysis and time series analysis. In each of these methods, discriminative features are extracted from EEG data and are passed to different classifiers to classify EEG brain signals. Transform-based techniques are among the most common EEG classifiers for extracting discriminative features from EEG signals. The objective in such methods is to present lower dimensional information in a compact form, where maximum data energy is presented in a few coefficients which are uncorrelated. After removing the indiscriminative features, these methods aid in extracting appropriate features.

The time series analysis, or entropy analysis, has been used to detect epileptic seizures, along with classification between control and schizophrenic subjects. This technique extracts different features, such as permutation entropy, sample entropy (SamEn) and approximate entropy (ApEn), for the classification of EEG signals. Spectral analysis of EEG signals has also been extensively used to extract features. This method uses signal rhythm analysis to classify EEG signals into, for example, alpha, beta, theta, gamma and delta frequencies, a power density spectrum, local minima and maxima, or the autoregressive moving average for the classification problem of EEG signals.

Time-frequency analysis of EEG signals has also been used for clinical EEG data to extract wavelet features from EEG patterns, providing, for example, a technique for epileptic seizure detection. In one study, various features were extracted from EEG signals, including wavelet-based features, fractal dimension (FD), SamEn and ApEn. After feature extraction, different classifiers were applied, including a decision tree, support vector machines (SVM), a k-nearest neighbor (k-NN) and a neural network (NN) to identify epileptic seizures. The study reported an accuracy of 99% by using wavelet and time-domain based features. However, only a small dataset was used in this study.

Other studies have employed different features based on complexity and entropy, such as FD, spectral entropy, ApEn and Lempel-Ziv complexity. Classification of EEG signals of schizophrenic patients were found to achieve an accuracy of 80-90% by using Adaboost and linear discriminant analysis (LDA) classifiers. In a further study, wavelet complexity and entropy features were extracted from EEG signals and non-linear classifiers were applied, including SVM and NN, to classify working memory (WM) loads. A classification accuracy between 90-96% was obtained for discriminating various WM loads. However, the EEG signals utilized in these studies were time locked. Further, the length of the EEG signals was relatively short compared against spontaneous EEG signals.

The above methods either use complicated and time-consuming feature extraction methods (e.g., ApEn, SamEn) or employ sophisticated classification techniques, such as kernel-based SVM and NN, and only yield acceptable classification accuracy when the data is clean. Specifically, these techniques are single-application specific and work only with clean EEG signals. Further, these techniques suffer from the "overfitting" problem; i.e., when they are applied to different datasets concerning the same problem, the classification may fail to fit additional data or predict future observations reliably. Thus, a method of classifying EEG signals solving the aforementioned problems is desired.

SUMMARY

The method of classifying raw electroencephalogram (EEG) signals uses a classification method based on nuclear features extracted as dominant singular values from an EEG signal segment using singular value decomposition (SVD) and a class means-based minimum distance classifier (CM-MDC) to classify a patient's EEG signals. The EEG signals are received from a set of EEG channels associated with the patient's brain (i.e., each EEG channel is associated with an electrode connected to the patient for recording EEG signals from the patient's brain). The set of EEG signals are represented as $x^1, x^2, x^3, \ldots, x^n$, where n represents a total number of the EEG channels. Particularly, an $i^{th}$ EEG signal segment (time $t_1$ to $t_d$) corresponding to the $i^{th}$ channel is $x^i$, where $x^i = [x_1^i(t), x_2^i(t_2), \ldots, x_d^i(t_d)]^T = [x_1^i, x_2^i, \ldots, x_d^i]$, and the set of EEG signals $x^1, x^2, x^3, \ldots, x^n$ correspond to an event. This EEG segment represents the brain state activated by the event and is treated as an instance. A mean EEG signal, $\bar{x}$, and a standard deviation of the set of EEG signals, std, are each calculated.

From the mean EEG signal, a set of zero-centered EEG signals are then calculated. An $i^{th}$ one of the zero-centered EEG signals, $y^i$, is calculated as $y^i = x^i - \bar{x}$ for $i = 1, 2, 3, \ldots, n$. From the zero-centered EEG signals and the standard deviation, a unit variance for each of the zero-centered EEG signals is then calculated, where an $i^{th}$ one of the unit variances, $\phi^i$, is calculated as $$\phi^i = \frac{y^i}{std}.$$

A nuclear matrix, N, is calculated as $N = A^T A$, where A is a matrix representing standardized component signals and is formed as $A = [\phi^1 \ \phi^2 \ \ldots \ \phi^n]$. Singular value decomposition is applied to the nuclear matrix to generate a set of singular values, such that $N = UDV^T$, where U and V are unitary matrices and D is a diagonal matrix formed from a set of singular values. An $i^{th}$ one of the singular values is represented as $\sigma_i$ for $i = 1, 2, 3, \ldots, n$, with $\sigma_1$ and $\sigma_2$ being defined as dominant singular values such that a nuclear feature vector, F, is defined as $F = [\sigma_1, \sigma_2]^T$.

The mean nuclear feature vectors, $C\mu_1$ and $C\mu_2$, respectively corresponding to first and second classes, $C_1$ and $C_2$, are calculated using training EEG signal segments. A class means-based minimum distance classifier (CMMDC) is used to classify an EEG signal segment into one of the two classes, $C_1$ or $C_2$. The CMMDC assigns an unknown EEG signal segment to the class for which distance between the class mean and its nuclear feature vector is a minimum. The distance used as a measure of similarity indicates that similarity is maximum if distance is minimum. Thus, a first distance, $d_1$, is calculated as $d_1 = |F - C\mu_1|$, where $C\mu_1$ is the mean nuclear feature vector of the first class, $C_1$, of a sample dataset. Similarly, a second distance, $d_2$, is calculated as $d_2 = |F - C\mu_2|$, where $C\mu_2$ is the mean nuclear feature vector of the second class, $C_2$, of the sample dataset.

The set of EEG signals of the patient is then classified as being in the second class, $C_2$, if $d_1 > d_2$. Otherwise, the set of EEG signals of the patient is classified as being in the first class, $C_1$. As an example, the sample dataset may be established through prior EEG readings of a sample set of test subjects measuring fluid intelligence. The first classification may then be high ability, with regard to fluid intelligence, and the second classification may be low ability. If $d_1 > d_2$, then the patient's EEG signals may be classified by the second classifier (i.e., low ability in this example), otherwise the patient's EEG signals may be classified by the first classification (i.e., high ability in this example).

These and other features of the present invention will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
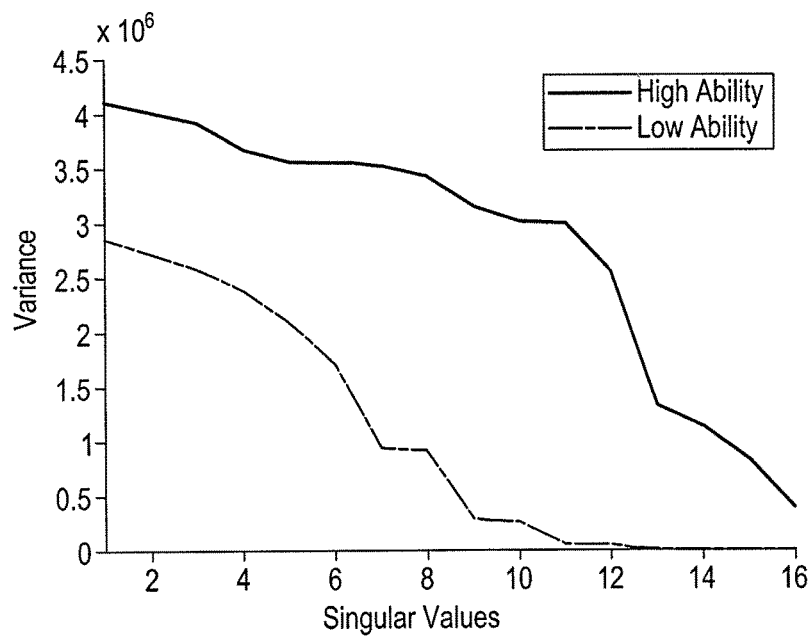
FIG. 1 is a plot of singular values, calculated by a method of classifying electroencephalogram (EEG) signals, with the data being obtained from clean EEG signals captured from frontal-left and frontal-right regions of a test subject.

A method of classifying electroencephalogram (EEG) signals uses a singular value decomposition (SVD) to extract nuclear features from EEG signals and a class means-based minimum distance classifier (CMMDC) to classify the nuclear features. The EEG signals are received from a set of EEG channels associated with an individual's brain (i.e., each EEG channel is associated with an electrode connected to the patient for recording EEG signals from the patient's brain). The nuclear features can be extracted from raw EEG signals i.e., EEG signals captured directly from the brain without any pre-processing. The projection of raw EEG signals captured from a certain brain region on a singular space by singular value decomposition (SVD) provides an amount of variances along different directions. Small value variances are due to artifacts and dominant (big value) variances represent the discriminative part of the signals. As such, dominant variances can be used to represent an event and a small number of dominant variances can be enough to discriminate two different events. As such, the extraction technique results in a feature space of small dimension, where the regions corresponding to different classes are well-separated. CMMDC can then be used to efficiently and reliably classify any unknown event.

The EEG signals are associated with a brain state activated by an event. From a mean EEG signal, a set of zero-centered EEG signals are calculated by transforming the signals, and from the zero-centered EEG signals and a standard deviation of the EEG signals, a unit variance of each component is calculated by dividing each signal component-wise with the standard deviation. The unit variances are used to establish a nuclear matrix, to which singular value decomposition is applied to generate a set of singular values. The mean nuclear feature vectors, $C\mu_1$ and $C\mu_2$, respectively corresponding to first and second classes, $C_1$ and $C_2$, are calculated using training EEG signal segments. A class means-based minimum distance classifier (CM-MDC) is used to classify an EEG signal segment into one of the two classes, $C_1$ or $C_2$. The CMMDC assigns an unknown EEG signal segment to the class for which distance between the class mean and its nuclear feature vector is a minimum. The distance used as a measure of similarity indicates that similarity is maximum if distance is minimum.

Feature extraction can be based on the nuclear norm, which is defined using singular values of a matrix as:

$$\|C\|_* = \sum_{i=1}^{n} \sigma_i(C), \quad (1)$$

where $\sigma_i$, $i=1, 2, 3, \ldots n$ are the singular values. It is known that nuclear norm is more discriminative and robust than the $L_1$-norm, the $L_2$-norm or the Frobenius norm. The nuclear norm has been employed for many pattern recognition tasks, such as robust PCA, low rank matrix recovery, and nuclear norm based 2-DPCA (N-2-DPCA). The reason that the nuclear norm outperforms the $L_1$-norm and the $L_2$-norm appears to be its basis of singular values. This indicates that singular values can be used to represent EEG brain signals. Based on this indication, singular values can be computed for the nuclear matrices of EEG signals measured from the same region corresponding to different brain states (events), as will be described in detail below.

The $i^{th}$ EEG signal segment (time $t_1$ to $t_d$) corresponding to the $i^{th}$ channel is represented as $x^i$, where $x^i = [x_1^i(t_1), x_2^i(t_2), x_3^i(t_3), \ldots, x_d^i(t_d)]^T = [x_1^i, x_2^i, x_3^i, \ldots, x_d^i]$; i.e., for purposes of clarity, time stamps have been removed in the representation. In the following, n is the number of electrodes placed on a particular brain region, and $x^1, x^2, x^3, \ldots, x^n$ represent the signals (i.e., channels) captured by the n electrodes during brain activation corresponding to an event; i.e., these signals represent the brain state activated by an event and are treated as an "instance". The mean, $\bar{x}$, and standard deviation, std, of these signals are respectively given by:

$$\bar{x} = \frac{1}{n}\sum_{1}^{n} x^i, \text{ and} \quad (2)$$

$$std = \sqrt{\frac{1}{n}\sum_{1}^{n}(x^i - \bar{x})^2}. \quad (3)$$

The signals are transformed so that they are zero-centered:

$$y^i = x^i - \bar{x}, i = 1, 2, 3, \ldots, n. \quad (4)$$

Each signal y is then divided component-wise by the standard deviation std so that each component has unit variance:

$$\phi^i = \frac{y^i}{std}, i = 1, 2, 3, \ldots, n. \quad (5)$$

Using the transformed signals, the following matrix is defined:

$$N = A^T A, \quad (6)$$

where $A = [\phi^1 \ \phi^2 \ \ldots \ \phi^n]$. The size of matrix N is n×n, and it represents a single event (e.g., high ability or low ability). The matrix N is referred to as the nuclear matrix. Using singular value decomposition (SVD), the matrix N is factorized as:

$$N = UDV^T, \quad (7)$$

where D is diagonal and the diagonal entries are the singular values $\sigma_i$, i=1, 2, 3, ..., n. $\sigma_1$ and $\sigma_2$ are defined as dominant singular values such that a nuclear feature vector, F, is defined as $F = [\sigma_1, \sigma_2]^T$.

For purposes of testing, the method of characterizing EEG signals was used by the present inventors for fluid intelligence level prediction. EEG signals were collected from 34 test subjects. Using a Raven's advanced progressive matrices (RAPM) test, the subjects were divided into two groups: low ability (LA) and high ability (HA), based on their intellectual abilities. The visual oddball cognitive task was then used to capture the neural activity of each subject. Target and standard stimuli were presented to the subjects. EEG signals were measured in the same region, corresponding to different brain states, or events. Two dominant singular values were selected to represent the EEG signals. The brain activation of each subject was captured as EEG signals from the following different brain regions: "TEMP", which includes temporal-left (TL) and temporal-right (TR) (with 8 channels); "FRONT", which includes frontal-left (FL) and frontal-right (FR) (with 16 channels); "CENT", which includes central-left (CL) and central-right (CR) (with 20 channels); "PERI", which includes parietal-left (PL) and parietal-right (PR) (with 18 channels); "OCCIP", which includes occipital-left (OL) and occipital-right (OR) (with 18 channels); and "ALL", which includes all regions (AR) (with 100 channels).

From the recorded EEG signals, two datasets for the classification of subjects into the LA and HA groups were prepared, based on their fluid intelligence levels: the "raw" dataset (RD) is data without any processing after recording of the signal, and the clean dataset (CD), made after recording by removing artifacts. The EEG trials related to each subject were segmented using a window having a duration of 600 msec, which contains a pre-stimulus period of 100 msec (i.e., the baseline) and a post-stimulus period of 500 msec.

For the CD, the data was cleaned by first removing muscular artifacts of high frequency, as well as removing the DC components by using a band pass filter (roll off 12 dB octave, 0.3-30 Hz). The trials which suffered from artifacts, such as eye movements and eye blinks, were rejected. For example, if the amplitude of the EEG signal of any trial was +90 μV, it was rejected. All recorded EEG signals were visually inspected and the channels, which had no contact in the phase of widespread drift, were removed. The spherical spline method was used to discard a trial if any bad channel was found. The nuclear features were extracted from raw and clean data using SVD based method. The discriminative features were input to the simple and efficient CMMDC to predict whether an individual belongs to LA or HA group in raw as well as clean data.

Figure 2:
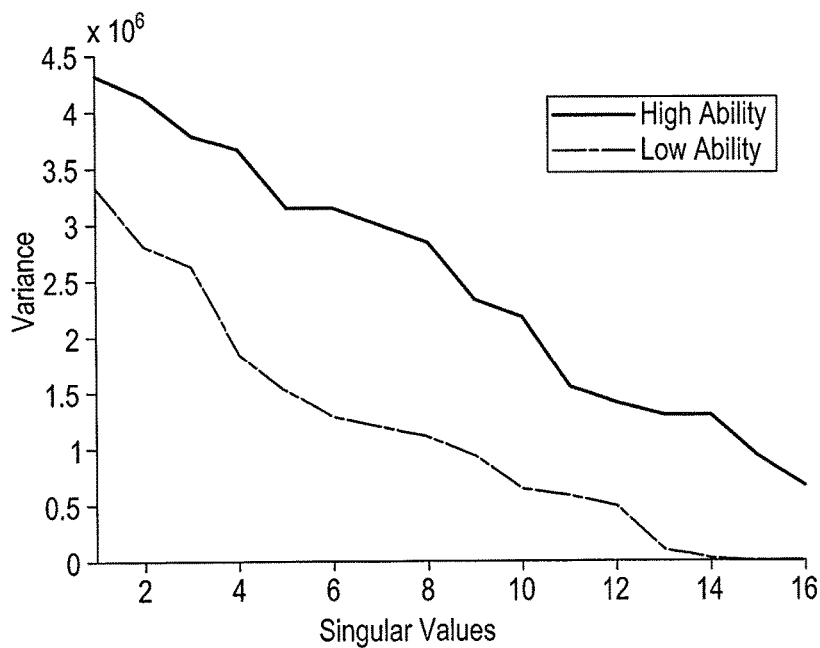
FIG. 2 is a plot of singular values, calculated by the method of classifying EEG signals, with the data being obtained from raw EEG signals captured from frontal-left and frontal-right regions of the test subject.
Figure 3:
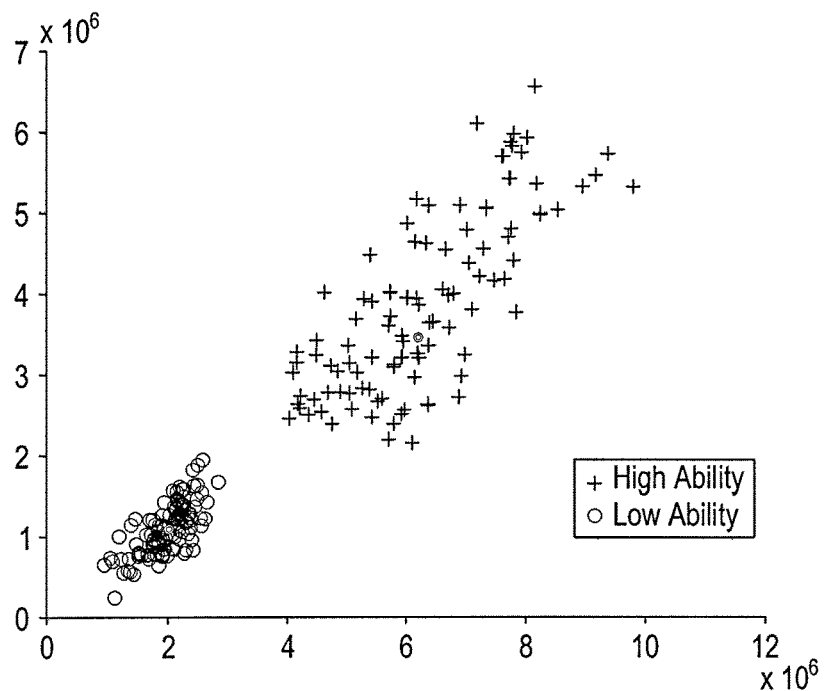
FIG. 3 is a plot of class data, shown for two different groups, using nuclear features calculated by the method of classifying EEG signals and extracted from clean EEG signals captured from frontal-left and frontal-right regions of a set of test subjects.
Figure 4:
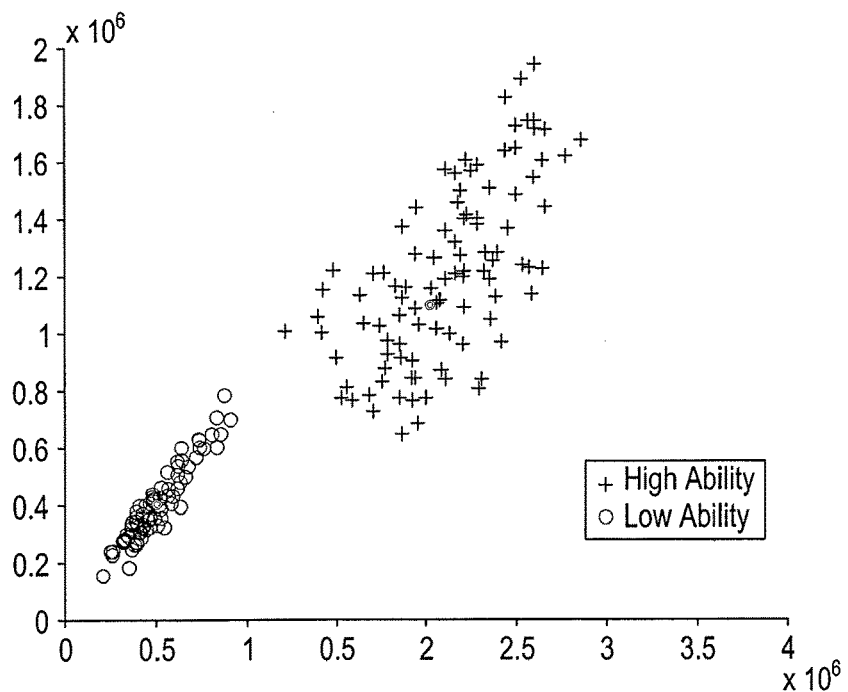
FIG. 4 is a plot of class data, shown for two different groups, using nuclear features calculated by the method of classifying EEG signals and extracted from raw EEG signals captured from frontal-left and frontal-right regions of the set of test subjects.

FIG. 1 shows a plot of singular values obtained from "clean" EEG signals captured from the "FRONT" (including FL and FR) region of a test subject, and FIG. 2 shows a plot of singular values obtained from "raw" EEG signals captured from the FRONT region of the test subject. These plots show that the singular values clearly discriminate the two events. As such, these can be used to differentiate the brain states corresponding to different events. Further, the plots show that the largest singular values are more discriminant. In view of this observation, the two largest singular values may be used to represent the brain states stimulated by different events. Further, in order to rule out the possibility that the discrimination shown in FIGS. 1 and 2 is only associated with these two particular examples, a number of additional examples of two events for both clean and raw data of the visual oddball task are shown in FIGS. 3 and 4. FIGS. 3 and 4 each plot EEG brain signals represented as the two largest singular values (represented as crosses for high ability and circles for low ability) for two different events. In FIG. 3, the results for the two separate groups (HA and LA) are shown for the two dominant nuclear features extracted from the clean EEG signal from the FRONT region. In FIG. 4, the results for the two separate groups (HA and LA) are shown for the two dominant nuclear features extracted from the raw EEG signal from the FRONT region. As shown, the two different events cluster together in two distinct regions of the feature space, which can be separated by a simple decision boundary. This observation leads to the conclusion that the two largest singular values can discriminate well for EEG brain signals corresponding to different events, and can be used as features to represent the events. These features are referred to as "nuclear features".

From FIGS. 3 and 4, it can be seen that data belonging to each class is clustered around the mean of its own class. These plots show that the examples related to two different events have high interclass variation and are clustered in separate regions of the feature space, which can be separated by simple decision boundary. Thus, a simple and efficient minimum distance classifier based on class means may be used to classify the nuclear features of the two classes (i.e., LA and HA).

The class means-based minimum distance classifier (CM-MDC) assigns a sample to the class for which distance between the sample and its mean is a minimum. The distance as a measure of similarity indicates that similarity is a maximum if distance is a minimum. The class means, $C\mu_1$ and $C\mu_2$, of both classes, $C_1$ and $C_2$ are first calculated in each dataset. Then, the distance, d, between each sample, x, and the mean of each class are calculated as:

$$d_1 = |F - C\mu_1|, \text{ and} \quad (13)$$

$$d_2 = |F - C\mu_2|. \quad (14)$$

If $d_1 > d_2$, then $x \in C_2$, otherwise $x \in C_1$.

The classification results on the two datasets CD and RD in two different brain regions, FRONT and PERI, are shown below in Tables 1 and 2. In Tables 1 and 2, AUC represents the area under the curve. Table 1 shows the results for the class means-based minimum distance classifier (CMMDC), and Table 2 shows the results for a support vector machines (SVM) classifier with a linear kernel, used for purposes of comparison.

TABLE 1

CMMDC results for the prediction of fluid intelligence level (LA vs. HA)

| Dataset | Brain Region | No. of Nuclear Features | No. of Channels | Accuracy | Sensitivity | Specificity | AUC | Testing Time (sec) |
|---|---|---|---|---|---|---|---|---|
| CD | FRONT | 02 | 16 | 100 | 100 | 100 | 1 | 5.4 |
|  | FRONT | 03 | 16 | 100 | 100 | 100 | 1 | 5.42 |
|  | PERI | 02 | 18 | 99.7 | 99 | 99 | 0.99 | 7.46 |
|  | PERI | 03 | 18 | 99 | 99.4 | 99 | 0.989 | 7.48 |
| RD | FRONT | 02 | 16 | 100 | 100 | 100 | 1 | 5.42 |
|  | FRONT | 03 | 16 | 100 | 100 | 100 | 1 | 5.45 |
|  | PERI | 02 | 18 | 99.1 | 99.5 | 98.9 | 0.98 | 7.47 |
|  | PERI | 03 | 18 | 99.5 | 99.8 | 99 | 0.99 | 7.49 |

TABLE 2

Support vector machines (SVM) classifier results for the prediction of fluid intelligence level (LA vs. HA)

| Dataset | Brain Region | No. of Nuclear Features | No. of Channels | Accuracy | Sensitivity | Specificity | AUC | Testing Time (sec) |
|---|---|---|---|---|---|---|---|---|
| CD | FRONT | 02 | 16 | 100 | 100 | 100 | 1 | 8.79 |
|  | FRONT | 03 | 16 | 100 | 100 | 100 | 1 | 8.802 |
|  | PERI | 02 | 18 | 99.4 | 99.6 | 98.2 | 0.99 | 10.93 |
|  | PERI | 03 | 18 | 99.1 | 99.3 | 98 | 0.987 | 10.95 |
| RD | FRONT | 02 | 16 | 100 | 100 | 100 | 1 | 8.86 |
|  | FRONT | 03 | 16 | 100 | 100 | 100 | 1 | 8.89 |
|  | PERI | 02 | 18 | 99 | 99.5 | 98.1 | 0.99 | 10.92 |
|  | PERI | 03 | 18 | 99.2 | 99.4 | 98.9 | 0.99 | 10.96 |

To evaluate the classification method, a 10-fold cross validation technique was used to test the performance of the system over different variations of the data. The given data was divided into 10 folds. Each fold was held out in turn and the remaining 9 folds were used to train and tune the system. After training and tuning the system, the left-over fold was used as an independent set to test the performance of the system. This process was repeated for each fold and the average performance values were calculated. The primary advantage of this technique was that the system was tested under various samples of data.

For purposes of evaluation, measures of accuracy, sensitivity and specificity were used, with each being defined as follows:

$$\text{Accuracy} = \frac{TP + TN}{TP + FN + TN + FP} \times 100; \quad (15)$$

$$\text{Sensitivity} = \frac{TP}{TP + FN} \times 100; \text{ and} \quad (16)$$

$$\text{Specificity} = \frac{TN}{TN + FP} \times 100, \quad (17)$$

where TP represents the number of true positives (e.g., the number of subjects actually belonging to LA which were predicted as belonging to LA), TN represents the number of true negatives (e.g., the number of subjects actually belonging to HA which were predicted as belonging to HA), FP represents the number of false positives (e.g., the number of subjects belonging to HA which were predicted as belonging to LA), and FN represents the number of false negatives (e.g., the number of subjects belonging to LA which were predicted as belonging to HA). The area under the receiver operating characteristic (ROC) curve was also used as a performance measure. In both datasets CD and RD, the total number of trials for the HA and LA groups were 551 and 482, respectively, and the channel length in each trial was 150 samples.

Figure 5:
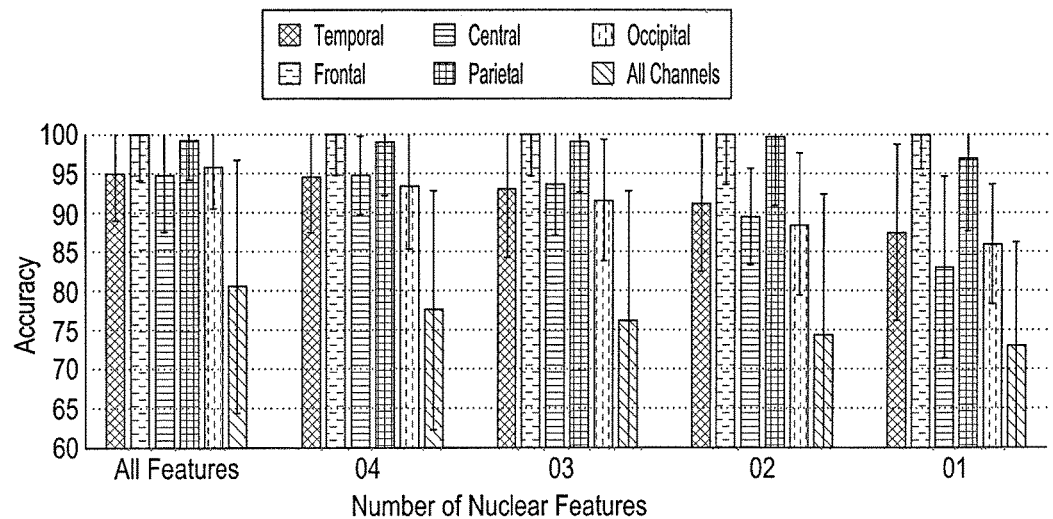
FIG. 5 is a graph showing accuracy of results for nuclear features calculated by the method of classifying EEG signals using a test sample of fluid intelligence clean data.
Figure 6:
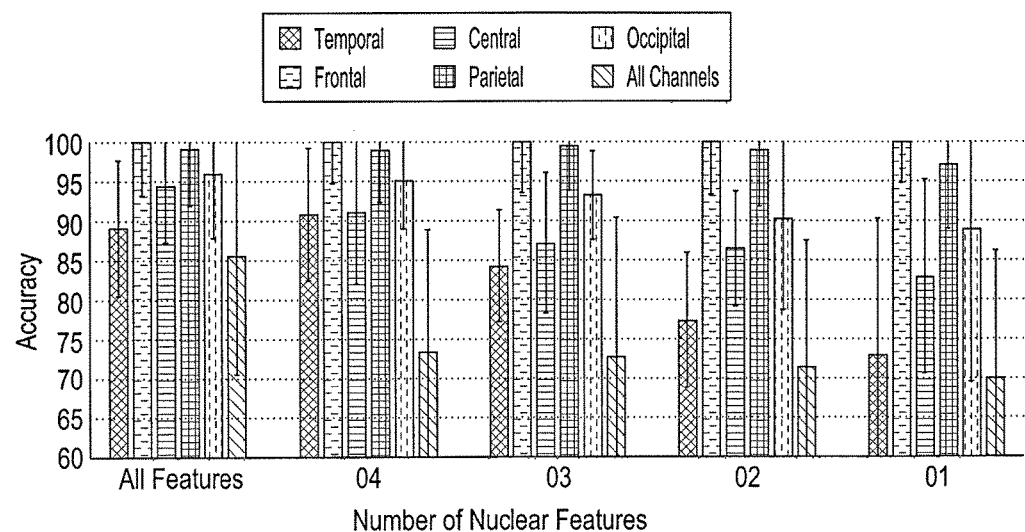
FIG. 6 is a graph showing accuracy of results for nuclear features calculated by the method of classifying EEG signals using a test sample of fluid intelligence raw data.

To analyze the performance of the classification method, six brain regions were considered; i.e., TEMP, FRONT, CENT, PERI, OCCIP and ALL, as described above. Both clean and raw EEG signals were captured for each region. In order to assess performance, the nuclear features were extracted using 8, 16, 20, 18, 18 and 100 channels captured from TEMP, FRONT, CENT, PERI, OCCIP and ALL, respectively. After extracting the nuclear features from the training data, class means were calculated and the test data was classified using CMMDC. The results of the classification are shown in FIGS. 5 and 6. FIG. 5 shows the classification results of nuclear features extracted using CMMDC with fluid intelligence clean data (CD). FIG. 6 shows the classification results of nuclear features extracted using CMMDC with fluid intelligence raw data (RD).

As shown in FIGS. 5 and 6, the different brain regions lead to different results. The best performance in assessing the fluid intelligence level is given by two regions out of the total six, namely the FRONT and PERI regions. The accuracy for the other regions is below 97%. These results show the dominance of the FRONT and PERI regions, which gave 100% and 99% accuracies, respectively, with two or three nuclear features. The detailed results for the two datasets CD and RD for these two brain regions are given above in Table 1. The results clearly show that nuclear features extracted from these two regions, the FRONT and the PERI regions, are discriminative and lead to the best results in classifying the subjects based on their fluid intelligence level (either LA or HA).

The results given above in Table 1 for CD and RD show that raw data gives results equivalent to those from clean data. In the case of the PERI region, the RD results in a relatively better performance than that of CD. For the PERI region, RD gives 99.5% accuracy and 99.8% sensitivity, whereas 99.0% accuracy and 99.4% sensitivity are obtained from CD. The CD gives slightly less accuracy and sensitivity than RD because some information is lost during cleaning of the EEG signals. Thus, it can be concluded that nuclear features are robust in representing the raw data.

To validate the usefulness of CMMDC, the SVM classifier with a linear kernel was also used for purposes of comparison. The detailed results with the SVM classifier are shown above in Table 2. The SVM classifier also gave 100% and 99% accuracies using nuclear features extracted from the FRONT and PERI regions, respectively. The results are the same as those obtained by using CMMDC, but CMMDC is more computationally efficient than SVM. Further, CMMDC is more memory efficient in that it does not need to keep the entirety of the training data, with only two class means being stored. This indicates that the CMMDC is more suitable for the classification of subjects based on their fluid intelligence levels.

Figure 7:
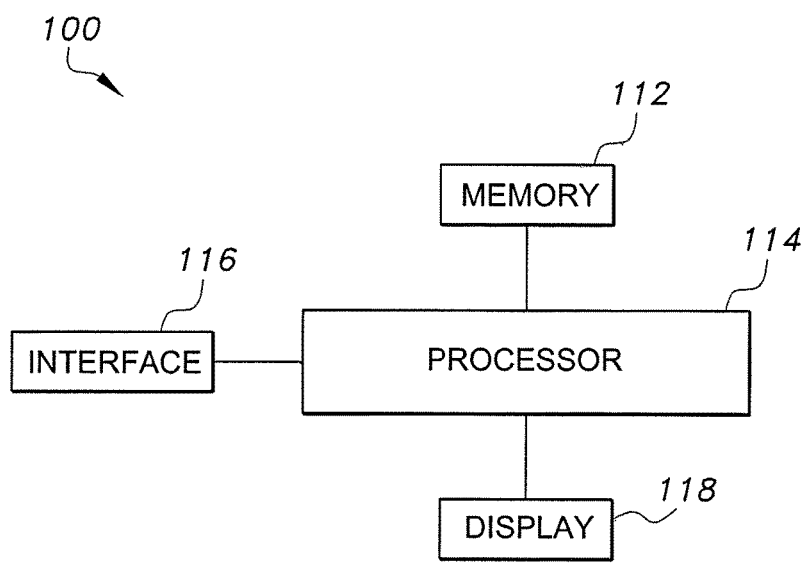
FIG. 7 is a block diagram illustrating system components for implementing the method of classifying EEG signals.

It should be understood that the above calculations may be performed by any suitable computer system, such as that diagrammatically shown in FIG. 7. Data is entered into system 100 via any suitable type of user interface 116, and may be stored in memory 112, which may be any suitable type of computer readable and programmable memory and is preferably a non-transitory, computer readable storage medium. Calculations are performed by processor 114, which may be any suitable type of computer processor and may be displayed to the user on display 118, which may be any suitable type of computer display.

Processor 114 may be associated with, or incorporated into, any suitable type of computing device, for example, a personal computer or a programmable logic controller. The display 118, the processor 114, the memory 112 and any associated computer readable recording media are in communication with one another by any suitable type of data bus, as is well known in the art.

Non-limiting examples of computer-readable recording media include non-transitory storage media, a magnetic recording apparatus, an optical disk, a magneto-optical disk, and/or a semiconductor memory (for example, RAM, ROM, etc.). Non-limiting examples of magnetic recording apparatus that may be used in addition to memory 112, or in place of memory 112, include a hard disk device (HDD), a flexible disk (FD), and a magnetic tape (MT). Non-limiting examples of the optical disk include a DVD (Digital Versatile Disc), a DVD-RAM, a CD-ROM (Compact Disc-Read Only Memory), and a CD-R (Recordable)/RW. It should be understood that non-transitory computer-readable storage media include all computer-readable media, with the sole exception being a transitory, propagating signal.

It is to be understood that the method of classifying EEG signals is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A computer implemented method of classifying raw electroencephalogram (EEG) signals by extracted features for the detection of high ability and low ability with regard to fluid intelligence in a patient, comprising the steps of:

placing a set of electrodes on the patient's scalp, wherein the placement includes at least the frontal-left and frontal-right and the parietal-left and the parietal-right brain regions;

providing a computer system, the computer system including a processor and a memory device having instructions stored thereon, wherein the instructions in response to executions by the processor cause the processor to:

receive a set of raw EEG signals directly from a set of EEG channels associated with the brain regions of the patient, wherein the raw EEG signals are associated with a brain state activated by an event, the set of raw EEG signals being represented as $x^1$, $x^2$, $x^3$, ..., $x^n$, where n represents a total number of the EEG channels;

calculate a mean EEG signal, $\bar{x}$, wherein the step of calculating the mean EEG signal comprises calculating $\bar{x}$ as $$\bar{x} = \frac{1}{n}\sum_{1}^{n} x^i;$$

calculate a standard deviation of the set of EEG signals, std, as $$std = \sqrt{\frac{1}{n}\sum_{1}^{n}(x^i - \bar{x})^2};$$

calculate a set of zero-centered EEG signals, wherein an $i^{th}$ one of the zero-centered EEG signals, $y^i$, is calculated as $y^i = x^i - \bar{x}$ for $i=1, 2, 3, ..., n$;

calculate a unit variance for each of the zero-centered EEG signals, wherein an $i^{th}$ one of the unit variances, $\phi^i$, is calculated as $$\phi^i = \frac{y^i}{std}$$

and constitutes a transformed signal; calculate a nuclear matrix, N, as $N=A^T A$, wherein A is a matrix representing the transformed signals and being formed as $A=[\phi^1 \phi^2 ... \phi^n]$, further wherein the matrix represents either high ability or low ability;

apply singular value decomposition to the nuclear matrix to generate a set of singular values, such that $N=UDV^T$, where U and V are unitary matrices and D is a diagonal matrix formed from a set of singular values, wherein an $i^{th}$ one of the singular values is represented as $\sigma_i$ for $i=1, 2, 3, ..., n$, $\sigma_1$ and $\sigma_2$ being defined as dominant singular values such that a nuclear feature vector, F, is defined as $F=[\sigma_1, \sigma_2]^T$;

use a class means based minimum distance classifier (CMMDC) to calculate a first distance, $d_1$, as $d_1=|F-C\mu_1|$, wherein $C\mu_1$ represents a mean nuclear feature vector of a first class of a sample dataset established through prior EEG readings of a sample set of test subjects measuring fluid intelligence;

use a class means based minimum distance classifier (CMMDC) to calculate a second distance, $d_2$, as $d_2=|F-C\mu_2|$, wherein $C\mu_2$ represents a mean nuclear feature vector of a second class of the sample dataset;

classify the set of raw EEG signals of the patient as being in the second class if $d_1>d_2$, and otherwise classifying the set of EEG signals of the patient as being in the first class, wherein the first class represents low ability and the second class represents high ability;

input the set of raw EEG signals directly from the set of EEG channels associated with the brain regions of the patient into a support vector machine (SVM) for generating a classification of the fluid intelligence of the brain regions being assessed and comparing the classification results with the CMMDC result to assess the accuracy of the CMMDC classification; and display the CMMDC classification result.

2. A system for classifying raw EEG signals by extracted features for the detection of high ability and low ability with regard to fluid intelligence in a patient, the system comprising:

a set of electrodes adapted to be placed on the patient's scalp, wherein the placement includes at least the frontal-left and frontal-right and the parietal-left and the parietal-right brain regions;

a computer system, the computer system including a processor and a computer readable medium for storing program instructions thereon that, when executed, cause the processor to:

receive a set of raw EEG signals directly from a set of EEG channels associated with the brain regions of the patient, wherein the raw EEG signals are associated with a brain state activated by an event, the set of raw EEG signals being represented as $x^1$, $x^2$, $x^3$, ..., $x^n$, where n represents a total number of the EEG channels;

calculate a mean EEG signal, $\bar{x}$, wherein the step of calculating the mean EEG signal comprises calculating $\bar{x}$ as $$\bar{x} = \frac{1}{n}\sum_{1}^{n} x^i;$$

calculate a standard deviation of the set of EEG signals, std, as $$std = \sqrt{\frac{1}{n}\sum_{1}^{n}(x^i - \bar{x})^2};$$

calculate a set of zero-centered EEG signals, wherein an $i^{th}$ one of the zero-centered EEG signals, $y^i$, is calculated as $y^i = x^i - \bar{x}$ for i=1, 2, 3, ..., n;

calculate a unit variance for each of the zero-centered EEG signals, wherein an $i^{th}$ one of the unit variances, $\phi^i$, is calculated as $$\phi^i = \frac{y^i}{std}$$

and constitutes a transformed signal;

calculate a nuclear matrix, N, as $N=A^TA$, wherein A is a matrix representing the transformed signals and being formed as $A=[\phi^1 \phi^2 \ldots \phi^n]$, further wherein the matrix represents either high ability or low ability;

apply singular value decomposition to the nuclear matrix to generate a set of singular values, such that $N=UDV^T$, where U and V are unitary matrices and D is a diagonal matrix formed from a set of singular values, wherein an $i^{th}$ one of the singular values is represented as $\sigma_i$ for i=1, 2, 3, ..., n, $\sigma_1$ and $\sigma_2$ being defined as dominant singular values such that a nuclear feature vector, F, is defined as $F=[\sigma_1, \sigma_2]^T$;

use a class means based minimum distance classifier (CMMDC) to calculate a first distance, $d_1$, as $d_1=|F-C\mu_1|$, wherein $C\mu_1$ represents a mean nuclear feature vector of a first class of a sample dataset established through prior EEG readings of a sample set of test subjects measuring fluid intelligence;

use a class means based minimum distance classifier (CMMDC) to calculate a second distance, $d_2$, as $d_2=|F-C\mu_2|$, wherein $C\mu2$ represents a mean nuclear feature vector of a second class of the sample dataset;

classify the set of raw EEG signals of the patient as being in the second class if $d_1>d_2$, and otherwise classifying the set of EEG signals of the patient as being in the first class, wherein the first class represents low ability and the second class represents high ability;

input the set of raw EEG signals directly from the set of EEG channels associated with the brain regions of the patient into a support vector machine (SVM) for generating a classification of the fluid intelligence of the brain regions being assessed and comparing the classification result with the CMMDC results to assess the accuracy of the CMMDC classification; and display the CMMDC classification result.

* * * * *